United States Patent

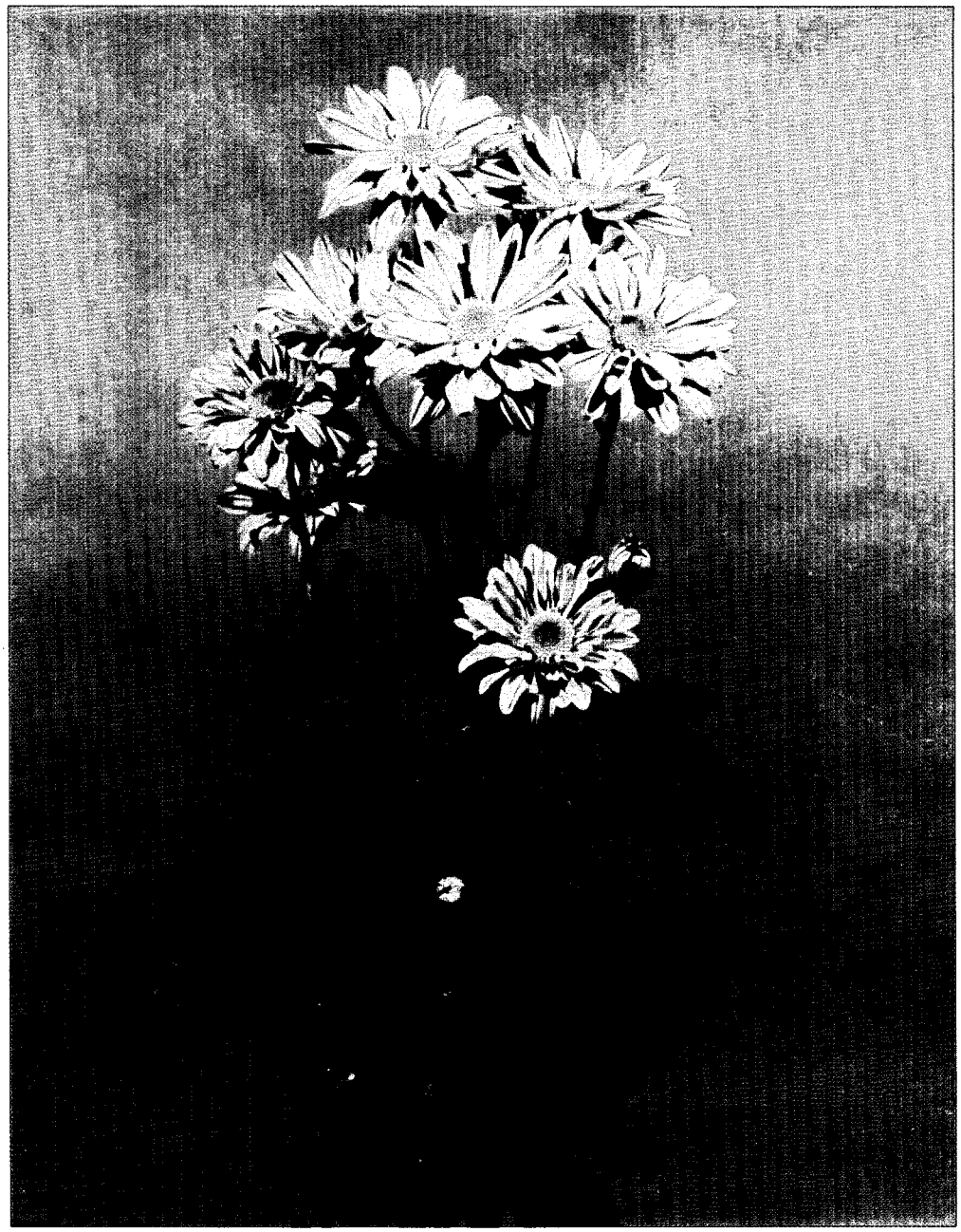

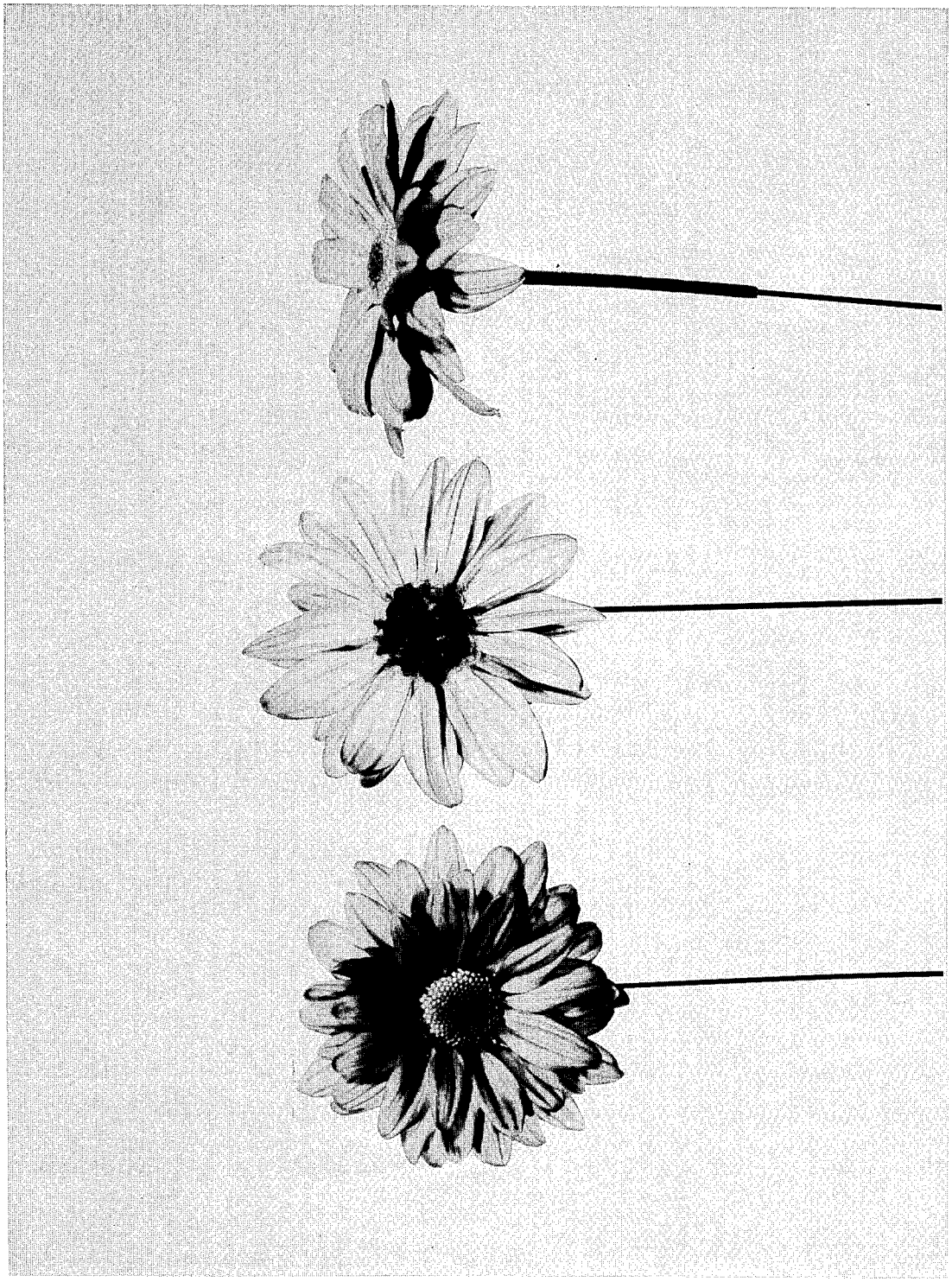

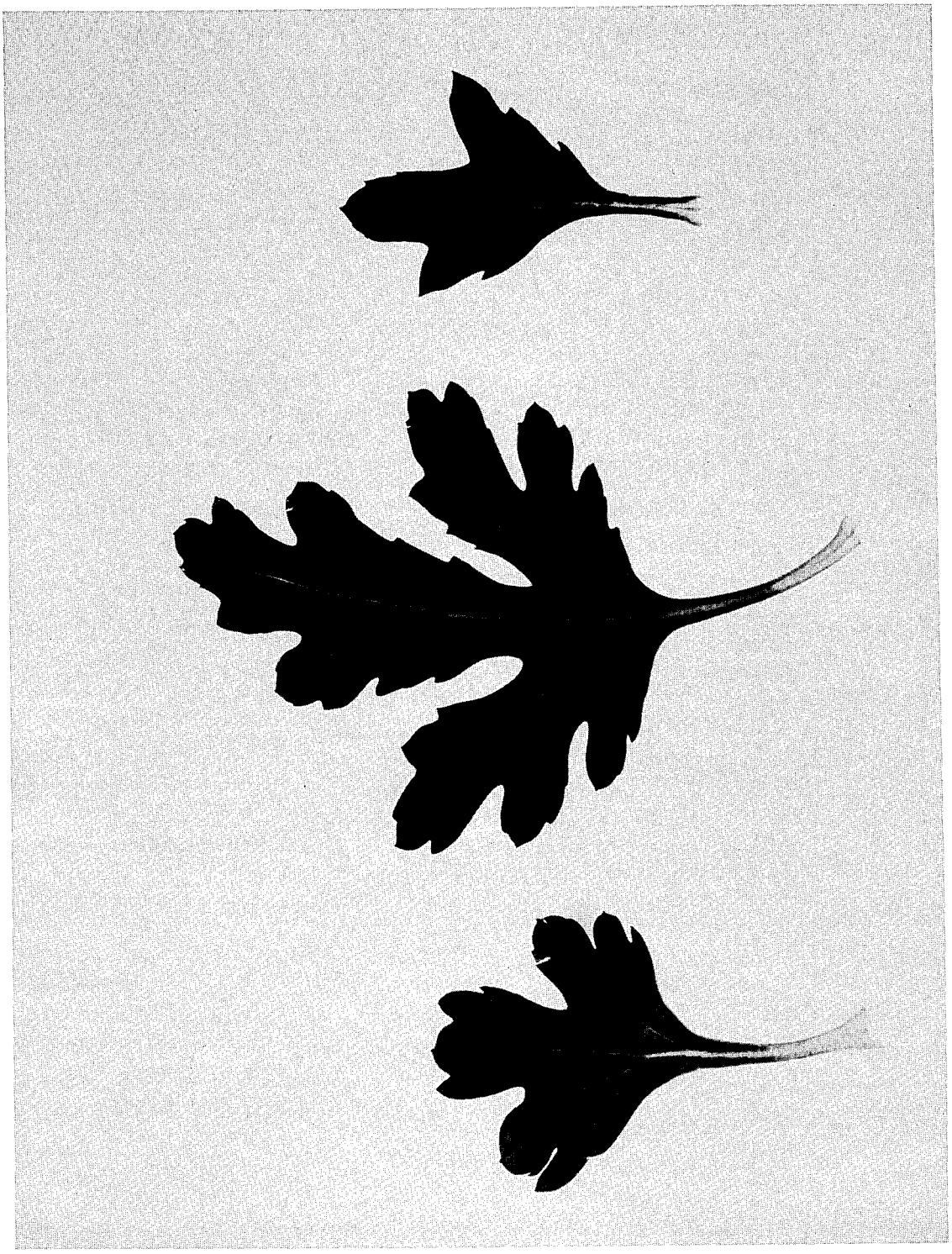

Plant Pat. 3,969

Patented Oct. 26, 1976

3,969

CHRYSANTHEMUM PLANT

Walter H. Jessel, Jr., Doylestown, and William E. Duffett, Akron, Ohio, assignors to Yoder Brothers, Inc., Barberton, Ohio

Filed Sept. 30, 1975, Ser. No. 619,918

Int. Cl.[2] A01H 5/00

U.S. Cl. Plt.—74 1 Claim

The present invention comprises a new and distinct cultivar of *Chrysanthemum morifolium*, Ramat., hereinafter referred to by the cultivar name Amber (#72208006).

Amber is a product of a planned breeding program which had the objective of creating new cultivars for use as a cut spray with daisy inflorescence type, with intense bronze and red-bronze inflorescence color, with eight and nine week flowering response period, and with resistance to color oxidation or anthocyanin breakdown under stress of high temperatures. Such traits in combination were not present in previously available commercial cultivars.

Amber was originated from a cross made in a controlled breeding program in Barberton, Ohio in 1971. The female, or seed parent, was #68210008 (unnamed seedling), a bronze daisy originated by the present inventors from a cross between Dramatic (#67079001; U.S. Plant Pat. No. 3,189) and Aglow (#65781001; U.S. Plant Pat. No. 3,212). The male, or pollen parent of Amber, was #70295008 (unnamed seedling), a pink daisy originated by the present inventors from a cross between Dramatic and Nimrod (#60096C02; unpatented; commercially available). Dramatic, Aglow, and Nimrod are all products of the breeding program of the present inventors.

Amber was discovered and selected as a flowering plant within the progeny of the stated cross by William E. Duffett and Walter H. Jessel, Jr. on Oct. 31, 1972 in a controlled environment in Barberton, Ohio.

The first act of asexual reproduction of Amber was accomplished when vegetative cuttings were taken from the initial selection in February, 1973 in a controlled environment in Barberton, Ohio by a technician working under formulations established and supervised by William E. Duffett and Walter H. Jessel, Jr. Horticultural examination of selected units initiated Nov. 18, 1973 has demonstrated that the combination of characteristics as herein disclosed for Amber are firmly fixed and are retained through successive generations of asexual reproduction.

Amber has not been observed under all possible environmental conditions. The phenotype may vary significantly with variations in environment such as temperature, light intensity, and daylength. The following observations, measurements, and comparisons describe plants grown in Barberton, Ohio under greenhouse environmental conditions which approximate those generally used in commercial practice, as described in Chart A and Chart B which appear at the end of the present specification.

The following traits have been repeatedly observed and are determined to be basic characteristics of Amber which in combination distinguish this chrysanthemum as a new and distinct cultivar:

(1) Flat inflorescence form.
(2) Daisy inflorescence type.
(3) Bronze ray floret color.
(4) Minimal inflorescence color oxidation during high temperature periods.

(5) Green disc floret color at immature, unopened stage.
(6) Minimal pollen development.
(7) Uniform nine week flowering response to photoperiodic short-day control.
(8) Diameter across face of inflorescence up to 3.25 inches at maturity.
(9) Tall plant height.
(10) Semi-upright branching pattern.
(11) Terminal spray formation during high temperature periods.

The accompanying photographic drawings show typical inflorescence and foliage characteristics of Amber with colors being as nearly true as possible with illustrations of this type. Sheet 1 is a color photograph of Amber. Sheet 2 is a black and white photograph showing three views of the inflorescence of Amber. Sheet 3 is a black and white photograph showing the foliage of Amber at three stages of growth.

Of the many commercial cultivars known to the present inventors, the most similar existing cultivars in comparison to Amber are Gay Marble (#54318H08; U.S. Plant Pat. No. 3,526), Red Dazzler (#65093A01; U.S. Pat. No. 3,523), and Dramatic. Reference is made to attached Chart C which compares certain characteristics of Amber with those same characteristics of the above mentioned cultivars. General comparisons are as follows:

(1) In comparison to Dramatic, Amber has different ray floret color, lower grade-out (Society of American Florists standards), taller plant height, and less ray floret color oxidation. The spray formation during high temperature periods and the flowering response period of Amber are similar to those of Dramatic.

(2) In comparison to Gay Marble, Amber has different ray floret color, less ray floret color oxidation, and more terminal spray formation during high temperature periods. The grade-out (SAF standards), plant height, and flowering response period of Amber are similar to those of Gay Marble.

(3) In comparison to Red Dazzler, Amber has different ray floret color, less ray floret color oxidation, lower grade-out (SAF standards), and more terminal spray formation during high temperature periods. The plant height, and the flowering response period of Amber are similar to those of Red Dazzler.

In the following description, color references are made to The Munsell Limit Color Cascade, 1972 edition. The color values were determined between 4:30 and 5:00 p.m. on June 27, 1975 under 160 foot candle light intensity at Barberton, Ohio.

BOTANICAL CLASSIFICATION:

*Chrysanthemum morifolium*, Ramat., cv Amber.

I. INFLORESCENCE

A. *Capitulum*

*Form:* flat.
*Type:* daisy.
*Permanence:* 11–14 days.
*Diameter across face:* 2.75 to 3.25 inches.

B. *Corolla of ray florets*

*Texture (adaxial):* glabrous.
*Appearance and form:* ligulate.
*Arrangement:* whorled on receptacle.
*Persistence:* resists shatter.
*Color (abaxial):* approximately 28–4 (streaked with 30–11) to 30–11.

*Color (adaxial):* approximately 28–3 to 29–4 streaked with 30–11.

*Veination:* prominent.
*Margin:* moderately serrated.

CHART A—AVERAGE GREENHOUSE CHRYSANTHEMUM ENVIRONMENTS USED FOR BARBERTON, OHIO

| Season | Temperatures used (° F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

C. *Corolla of disc florets*

*Appearance and form:* gamopetalous; tubular; 5-lobed.
*Color:* 23–10 to 27–6.

D. *Reproductive organs*

*Androecium:* present disc florets only; syngenesious stamen; scant pollen.
*Gynoecium:* present both ray and disc florets; inferior, bicarpellate ovary; single style; 2-lobed stigma.

II. PLANT

A. *General appearance*

Semi-upright; tall height.

B. *Duration and texture*

Perennial; herbaceous.

C. *Foliage*

*Color (abaxial):* 21–14 to 21–15.
*Color (adaxial):* 21–13 overcast with white.
*Shape:* spatulate; deeply lobed.
*Texture:* glabrous.
*Arrangement:* alternate.

CHART B

INTENSITY OF DIRECT SOLAR RADIATION

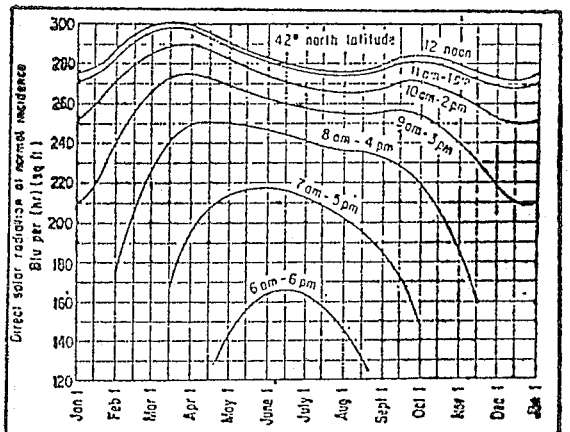

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF AMBER, DRAMATIC, GAY MARBLE AND RED DAZZLER

| Cultivar | Ray floret color | SAF gradeout | Plant height | Color retention | Spray formation during high temperatures | Flowering response period |
|---|---|---|---|---|---|---|
| Amber | Bronze | Medium | Tall | Good | Terminal | 9 weeks. |
| Dramatic | Golden bronze | High | Medium | Fair | do | Do. |
| Gay marble | Light orange bronze | Medium | Tall | Poor | Compound | Do. |
| Red Dazzler | Red bronze | High | do | Fair | do | Do. |

NOTE.—Comparisons made of plants grown in a greenhouse in Barberton, Ohio, under conditions as described in Chart A and Chart B.

We claim:

1. A new and distinct cultivar known by the cultivar name Amber and particularly characterized by the combined features of flat inflorescence form; daisy inflorescence type; bronze ray floret color; minimal inflorescence color oxidation during high temperature periods; green disc floret color at immature, unopened stage; minimal pollen development; uniform nine week flowering response to photoperiodic short-day control; diameter across face of inflorescence up to 3.25 inches at maturity; tall plant height; semi-upright branching pattern, and terminal spray formation during high temperature periods.

No references cited.

ROBERT E. BAGWILL, Primary Examiner